US00PP13130P2

(12) United States Plant Patent
Noodelijk

(10) Patent No.: US PP13,130 P2
(45) Date of Patent: Oct. 29, 2002

(54) CHRYSANTHEMUM PLANT NAMED 'REGGIE YELLOW'

(75) Inventor: Robert Noodelijk, Woubrugge (NL)

(73) Assignee: Chrysanthemum Breeders Association N.V. (NL)

( * ) Notice: Subject to any disclaimer, the term of this patent is extended or adjusted under 35 U.S.C. 154(b) by 0 days.

(21) Appl. No.: 09/562,138

(22) Filed: May 1, 2000

(51) Int. Cl.[7] ..... A01H 5/00
(52) U.S. Cl. ..... Plt./295
(58) Field of Search ..... Plt./295

(56) References Cited

PUBLICATIONS

UPOV–ROM GTITM Computer Database 2001/01, Feb. 6, 2001 GTI Jouve Retrieval Software, Ciation for 'REGGIE YELLOW'.*

* cited by examiner

*Primary Examiner*—Bruce R. Campell
*Assistant Examiner*—Annette Para

(57) ABSTRACT

A Chrysanthemum plant named "REGGIE YELLOW" characterized by its small sized blooms with yellow ray-florets and yellow-green disc florets.

2 Drawing Sheets

RELATED CULTIVARS

"REGGIE YELLOW" is related to "REGGIE" (U.S. application Ser. No. 09/561,931) and "REGGIE PINK" (U.S. application Ser. No. 09/561,930). Both are color mutants of "REGGIE".

BACKGROUND OF THE INVENTION

"REGGIE YELLOW" is a product of a breeding-program which had the objective of creating new chrysanthemum cultivars with a anemone type flower, a 7 week response and a medium plant height. The new plant of the present invention comprises a new and distinct cultivar of chrysanthemum plant that is a natural occuring sport of a parent chrysanthemum named "REGGIE". A comparison with parent chrysanthemum "REGGIE" is also made in this application. The new cultivar was discovered as a whole plant mutation in May 1995 by Rob Noodelijk in a controlled environment (greenhouse) in Rijsenhout Holland. The first act of asexual reproduction of "REGGIE YELLOW" was accomplished when vegetative cuttings were taken from the initial selection in July 1995 in Rijsenhout Holland.

SUMMARY OF THE INVENTION

The present invention is a new and distinct variety of chrysanthemum bearing small sized blooms with yellow ray-florets and yellow and green cushion.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
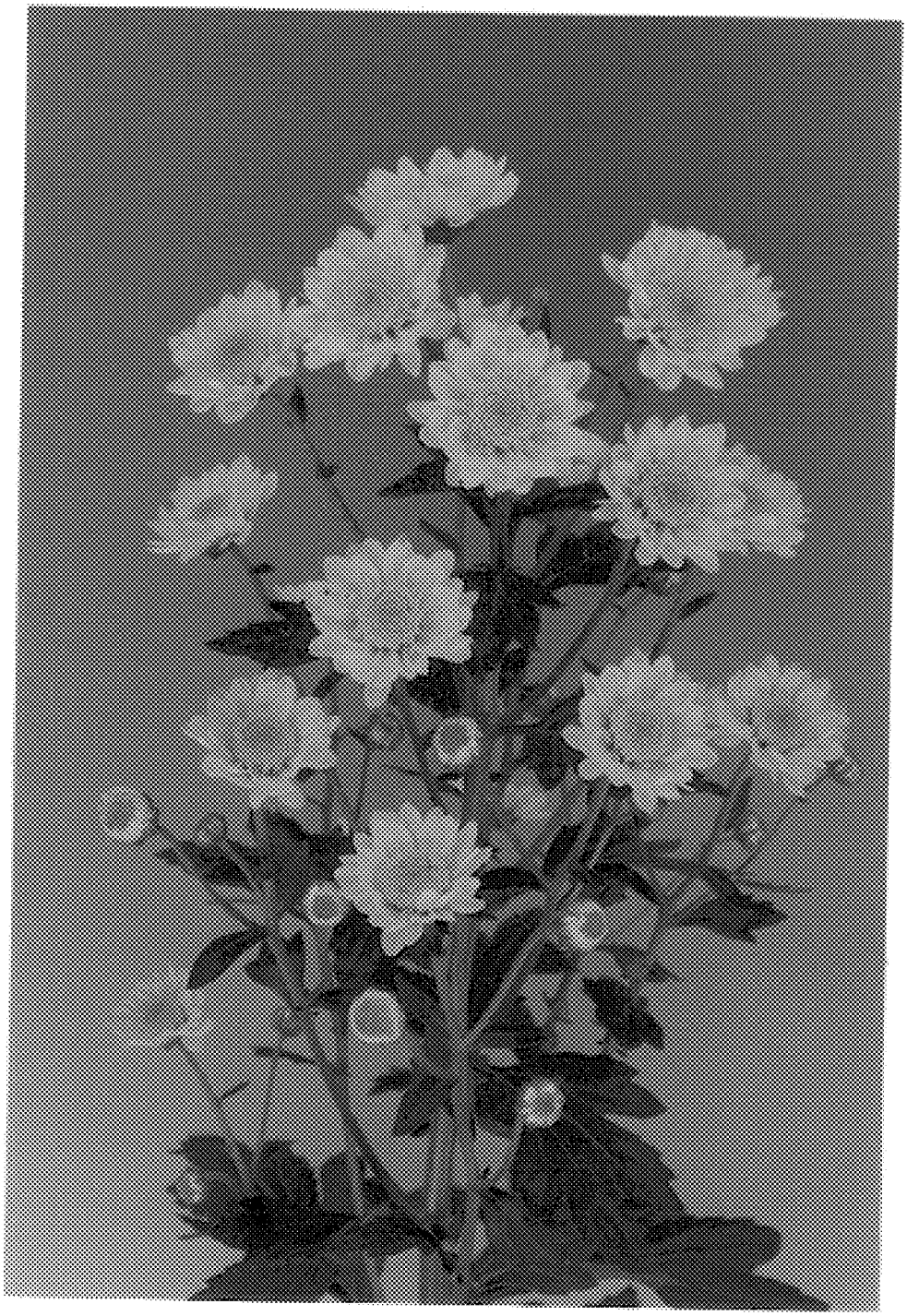
FIG. 1 shows a plant of the cultivar in full bloom.
Figure 2:
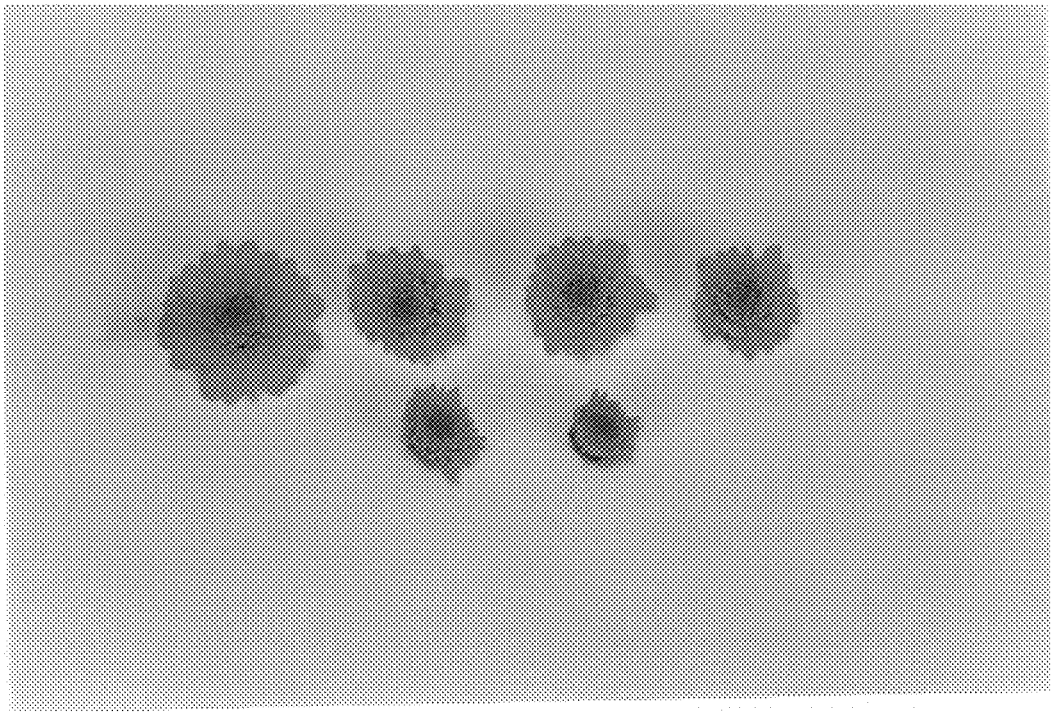
FIG. 2 shows the various stages of bloom of the new cultivar.
Figure 3:
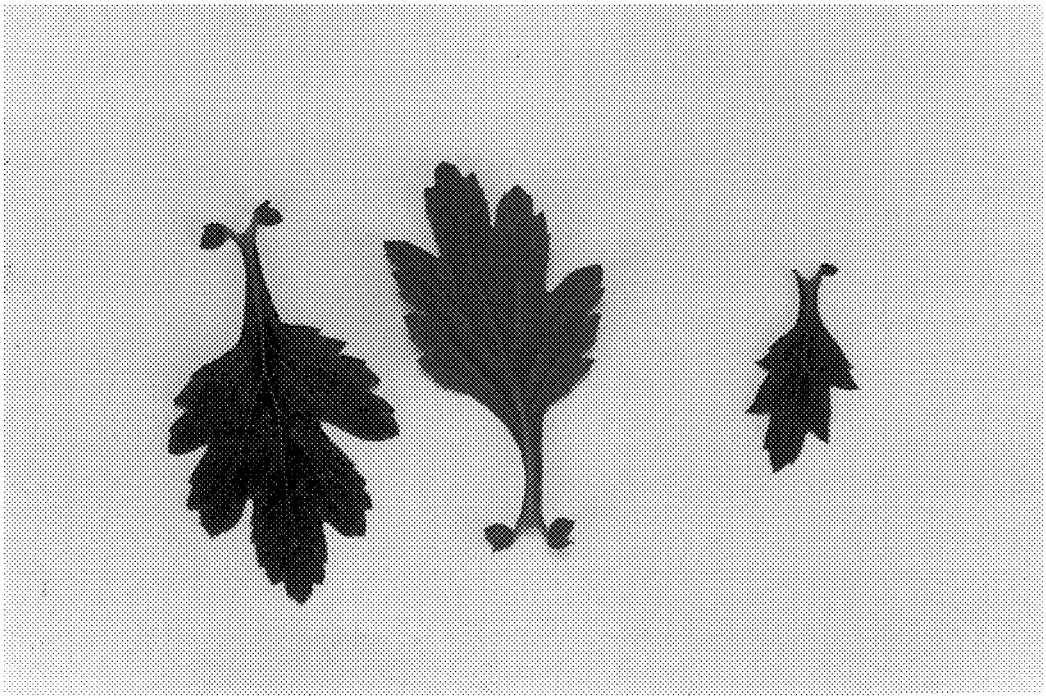
FIG. 3 shows the foliage of the new cultivar.

This new variety of chrysanthemum is of the botanical classification *Dendranthema grandiflora*. The observations and measurements were gathered from plants grown in a greenhouse in Rijsenhout Holland in a photo-periodic controlled crop under conditions generally used in commercial practice. The greenhouse temperatures during this crop were at day-time between 18° C. and 25° C. and at night 20° C. The photo-periodic response time in this crop was 47 days after an average of eight long days. The age of the observed plant was thus 55 days. After this long day period to flowering growth retardants were applied 6 times in an average dose of 1.5 gram/liter water. The plants were observed (directly) during the flowering of this crop. No tests were done on disease or insect resistance or susceptibility. No tests were done on cold or drought tolerance. This new variety produces small sized blooms with yellow ray-florets and yellow and green cushion blooming on the plant for 5 weeks. This new variety of chrysanthemum has been found to retain its distinctive characteristics throughout successive propagations however the phenotype may vary significantly with variations in environment such as light intensity and temperature. To show the phenotype as described "REGGIE YELLOW" can be planted without assimilation lightning (high pressure sodium lamps) between week 50 and week 40 of the next year under greenhouse conditions in Holland. With assimilation light (minimum level 2500 lux) it can be planted year round under greenhouse conditions in Holland.

From the cultivars known to inventor the most similar existing cultivar in comparison to "REGGIE YELLOW" is "REGGIE". When "REGGIE" and "REGGIE YELLOW" are being compared the following differences and similarities are noticed: The differences of REGGIE and "REGGIE YELLOW" is 1) the ray-floret color. For which characteristics "REGGIE YELLOW" has been selected out of REGGIE. 2) "REGGIE" is white, "REGGIE YELLOW" is yellow. All other characteristics of REGGIE and "REGGIE YELLOW" are similar.

The following is a description of the plant and characteristics that distinguish "REGGIE YELLOW" as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 1995.

Botanical Description of CULTIVAR "REGGIE YELLOW"

Bud:
*Size.*—Small, cross-section 1.0 cm, Height 0.6 cm.
*Outside color.*—Yellow 12 B.
*Involucral bracts.*—2 rows, length 7 mm, width 3 mm.
*Involucral bracts among disc-florets.*—Not present.
*Involucral bracts color.*—Yellow-green 144 A.

Bloom:
*Type.*—Anemone.
*Height.*—Flat (2.5 cm).
*Size.*—Small.
*Fully expanded.*—3.0–4.0 cm.
*Number of blooms per stem.*—Approx 16 blooms per branch.
*Performance on the plant.*—21 days.
*Seeds.*—Not produced.

CULTIVAR "REGGIE YELLOW"

Fragrance: Typical chrysanthemum.

Color:
*Center of the flower (disc-florets).*—Immature Yellow 14 A and green in the center, Mature almost completely Yellow 14 A.
*Color of upper surface of the ray-florets.*—Yellow 13 B.
*Color of the lower surface of the ray-florets.*—Yellow 13 C.
*Tonality from distance.*—A small yellow anemone with a yellow and green cushion.
*Discoloration to color.*—Ray-florets to yellow 13C.

Ray florets:
*Texture.*—Upper and under side smooth.
*Number.*—32–36 (2 rows).
*Cross-section.*—Concave.
*Longitudinal axis of majority.*—Incurving.
*Length of corolla tube.*—Very short.
*Ray-floret margin.*—Entire.
*Ray-floret length.*—1.8–2.0 cm.
*Ray-floret width.*—0.7–0.9 cm.
*Ratio length/width.*—Low.
*Shape of tip.*—Rounded.

Disc florets:
*Disc diameter.*—1.2–1.4 cm.
*Distribution of disc florets.*—Numerous clearly visible at all stages of flowering.
*Shape.*—Petaloid.
*Color.*—Yellow 14 A.
*Receptacle shape.*—Domed raised.

Reproductive organs:
*Stamen (present in disc florets only).*—Thin, 4 mm in length.
*Number of stamen.*—Grown together as one.
*Stamen color.*—Yellow-green 144 B.
*Pollen.*—None.
*Styles (present in both ray and disc florets).*—Thin.
*Style color.*—Yellow-green 144 B.
*Style length.*—5 mm.
*Stigmas.*—Yellow-green 144 B.
*Stigma width.*—2 mm.
*Ovaries.*—Enclosed in calyx.

Plant:
*Form.*—A spray mum meant for use as a cut flower.
*Growth habit.*—Upright.
*Growth rate.*—Moderate.
*Height.*—100–105 cm.
*Internodes.*—2.0–2.5 cm.
*Spray formation.*—Pyramidal.
*Stem color.*—Yellow-green 144 A.
*Stem strength.*—Medium.
*Stem brittleness.*—Present.
*Stem anthocyanin coloration.*—Present, with a slight layer of greyed-red.
*Peduncle length.*—Near the top 10 cm, near the middle 14 cm, near the bottom 18 cm.
*Peduncle color.*—Yellow-green 144 A.
*Flowering response (photo-periodic controlled crop, not natural season).*—47 days.

Foliage:
*Color.*—Upper side green 137 A. Under side green 137 B.
*Size.*—Medium; length 6.5 cm, width 5.5 cm.
*Quantity (number per single stem).*—28–32.
*Shape.*—Ovate.
*Texture upper side.*—Glabrous.
*Texture under side.*—Pubescent.
*Venation arrangement.*—Palmate.
*Shape of the margin.*—Serrated.
*Shape of base of sinus between lateral lobes.*—Round.
*Margin of sinus between lateral lobes.*—Converging.
*Shape of base.*—Attenuate.
*Apex.*—Mucronate.

TABLE 2

Differences with the comparison varieties

| | "REGGIE YELLOW" | "REGGIE" | "REGGIE PINK" | DARK |
|---|---|---|---|---|
| Ray-floret color | Yellow 13 B | White 155 D | Red-purple A | 70 |

I claim:

1. A new and distinct variety of chrysanthemum plant as described and illustrated.

* * * * *